United States Patent
Friedrichs et al.

(10) Patent No.: US 7,041,062 B2
(45) Date of Patent: May 9, 2006

(54) DEVICE AND METHOD FOR PRODUCING RESPIRATION-RELATED DATA

(75) Inventors: Arnd Friedrichs, Jena (DE); Fridolin Voegeli, Thalwil (CH)

(73) Assignee: Friendly Sensors AG, Jena (DE)

( * ) Notice: Subject to any disclaimer, the term of this patent is extended or adjusted under 35 U.S.C. 154(b) by 0 days.

(21) Appl. No.: 10/380,723

(22) PCT Filed: Sep. 17, 2001

(86) PCT No.: PCT/EP01/10696

§ 371 (c)(1),
(2), (4) Date: Jul. 16, 2003

(87) PCT Pub. No.: WO02/22017

PCT Pub. Date: Mar. 21, 2002

(65) Prior Publication Data

US 2004/0097823 A1    May 20, 2004

(51) Int. Cl.
*A61B 5/08* (2006.01)
(52) U.S. Cl. ....................... 600/534; 600/529
(58) Field of Classification Search ........ 600/529–538, 600/588, 587, 591
See application file for complete search history.

(56) References Cited

U.S. PATENT DOCUMENTS

| | | | | |
|---|---|---|---|---|
| 3,268,845 A | * | 8/1966 | Whitmore | 338/47 |
| 4,308,870 A | * | 1/1982 | Arkans | 600/382 |
| RE32,180 E | * | 6/1986 | Lewiner et al. | 600/534 |
| 4,889,131 A | * | 12/1989 | Salem et al. | 600/484 |
| 4,960,118 A | * | 10/1990 | Pennock | 128/200.24 |
| 4,989,612 A | * | 2/1991 | Fore | 600/534 |
| 5,107,855 A | * | 4/1992 | Harrington et al. | 600/534 |
| 5,448,996 A | * | 9/1995 | Bellin et al. | 600/574 |
| 5,588,439 A | * | 12/1996 | Hollub | 600/534 |
| 5,701,370 A | * | 12/1997 | Muhs et al. | 385/13 |
| 5,730,145 A | * | 3/1998 | Defares et al. | 600/595 |
| 5,935,061 A | * | 8/1999 | Acker et al. | 600/304 |

* cited by examiner

*Primary Examiner*—Robert L. Nasser
(74) *Attorney, Agent, or Firm*—Bachman & LaPointe, P.C.

(57) ABSTRACT

An apparatus for producing data concerning the respiration-related movements of the abdominal wall and/or the thorax of a person. The device comprises at least one first pair of sensor units (12, 14), which are configured for detachably fixing on the skin in an area of the person's thorax or abdomen, a first distance (1) apart; and a measuring device (20) which is connected to said first pair of sensor units and which is configured for detecting signals of the sensor units that can be evaluated electrically and for producing a distance signal corresponding to the first distance (1) and to changes in the same. Connected downstream of the measuring device is an evaluation device (22, 28) which is configured for evaluating pulsed and/or wave-shaped changes in the first distance signal, in such a way that periodical signal changes of a frequency in the range of 0.05 to 0.1 Hz are detected, distinguished from the periodical changes in the first distance signal that are due to the human heartbeat in terms of frequency, amplitude or signal shape and output in the form of a respiration display signal that can be displayed and further processed electronically.

25 Claims, 6 Drawing Sheets

DEVICE AND METHOD FOR PRODUCING RESPIRATION-RELATED DATA

BACKGROUND OF THE INVENTION

The present invention relates to an apparatus and a method for producing measurement data concerning respiration-related movements of the abdominal wall and/or the thorax of a person. In particular, the present invention relates to a technical teaching the subject of which is the specified detection and monitoring of the respiratory activity of a person.

Breathing in (inspiration) is known to take place through expansion of the thoracic-pulmonary space by the respiratory muscles and through the resulting development of an alveolar partial vacuum in the expanding lung, leading to an inflow of air until pressure is equalized. Breathing out (expiration) takes place predominantly through a passive contraction of the thoracic space by a lowering of the thoracic cage and by an elasticity-related volumetric reduction (retraction) of the lung whereby air flows out as a result of the production of relative alveolar overpressure. Typical disorders of this human breathing process result, for example, from a reduction in lung elasticity or through narrowing of the apertures of the bronchial branches (restrictive or obstructive ventilation disorders), and from possible disorders of the respiratory centre, of diffusion or blood circulation in the lung.

Diaphragmatic respiration is the component of respiration resulting from contraction of the diaphragm (approx. two-thirds of breathing volume).

Attempts to detect and measure a respiration-related expansion of the thoracic and abdominal area during respiration in humans are known from the prior art. Sensors used typically for this purpose operate on piezoelectric principles and generate a comparatively low voltage as the output signal, a force being exerted on such a sensor through the respiration-related expansion of the thoracic or abdominal area during a breathing movement. By suitable processing a respiration signal is generated from a voltage signal produced thereby.

Other systems known from the prior art operate on an impedance principle, i.e. by making use of suitable resistor elements the electrical resistance of which changes through (respiration-related) movements of the thorax or the abdominal wall; in particular strain gauges or suchlike sensors are used for this purpose.

Known approaches of this kind have, however, the disadvantage that only a general detection of human breathing signals is possible, the quality and resolution of the electronic signal obtained normally being insufficient to permit monitoring of further body parameters at acceptable cost and without separate, additional sensors.

In view, in particular, of an inherent biological connection between respiration and cardiac activity it would therefore be desirable to be able to monitor both parameters simultaneously at low cost, and in particular with the use of only one sensor or one sensor arrangement. The same applies to the movement or activity of the person, as could be desirable in particular in the field of the observation of sporting activities.

It is therefore the object of the present invention to provide an apparatus for generating measurement data concerning respiration-related movements of the abdominal wall and/or the thorax of a person which is improved with respect to signal resolution and measurement accuracy in generating a respiration display signal and which therefore also offers, in particular, possibilities of detecting from this respiration display signal further parameters or superposed signals, and creates the possibility of generating with the same sensor system, in addition to data derived from respiratory movement, further data corresponding to other body parameters and functions, including heartbeat.

SUMMARY OF THE INVENTION

The foregoing object is achieved by an apparatus for generating measurement data concerning respiration-related movements of the abdominal wall and/or the thorax of a person, comprising at least one first pair of sensor units which are configured for detachable fixing on the skin on a thoracic or abdominal area of the person and are spaced apart by a first distance, and comprising a measuring device connected to the first pair of sensor units and configured for detecting signals of the sensor units which are capable of electrical evaluation and for generating a first distance signal corresponding to said first distance and changes in same, wherein an evaluation unit is connected to the output of the measuring device and is so configured for evaluating pulsed and/or waveform changes of the first distance signal that periodic signal changes of a frequency in the range between 0.05 and 0.1 Hz can be detected, distinguished in terms of frequency, amplitude or signal form from periodic changes of the first distance signal caused by the human heartbeat and outputted as a respiration display signal which can be electronically displayed or further evaluated. The object is further achieved by a method comprising the steps of continuous measurement of a first distance between two first sensors attached on the skin of the person on a thoracic or abdominal area, evaluation of electronic signal changes in the first measurement signal corresponding to changes in the first distance, and outputting of a respiration display signal as a reaction to a periodical signal change in the range between 0.1 and 0.5 Hz.

The present invention for data acquisition concerning respiration-related movements of the abdominal wall and/or the thorax of a person makes use in an inventively advantageous manner of the principle of data acquisition by measuring the distance between a pair of sensor units, changes in the distance between the sensors of the kind induced by the respiration-related movements to be detected generating the first distance signal according to the invention, which can be appropriately evaluated. In this context the fixing of the sensors to the skin is to be understood as a fixing of the sensors above the skin or body surface in such a way that a change in the distance between them can be detected from a pair of measuring points; it is therefore also provided in particular according to the invention to attach the sensors to the skin via an intermediate layer—a garment, a fabric or the like.

This principle for generating the first distance signal corresponds to that described in German Patent Application No. 42 14 523 and is realized in a manner known as such by means of a transmitter-receiver system based on ultrasonic or electromagnetic waves; with regard to an electronic constructional implementation of the distance measurement means the above-mentioned Patent/Patent Application DE 42 14 523 is to be regarded as included in its entirety in the present Application and as forming part of the invention.

The principle of ultrasonic distance measurement whereby the differences in travel time of the ultrasonic signal between the sensor units are measured and evaluated has proved advantageous for the implementation of measurement data generation concerning respiration-related movements according to the invention; alternatively, it is possible to utilize and evaluate phase differences between the transmitted and received signal.

According to the present invention this known technology now finds application to the particular requirements of measuring a respiration-related movement of the abdominal wall and/or the thorax, the distance-dependent capture of measurement data relating to movements of the thorax having proved to be especially reliable and accurate in conjunction with the evaluation unit provided according to the invention. Advantageously, this procedure according to the invention not only permits (general) testing for the presence of a breathing movement (which takes place according to the invention through the signal-related or time-related discrimination made possible by the evaluation unit), but the invention also offers the possibility—especially if a plurality of pairs of sensors are provided according to a refinement of the invention—of detecting with high resolution the thoracic movements induced by respiratory movements together with their temporal, local and spatial propagations, thereby making possible an investigation as to whether a respiratory process as such might possibly be pathological (if, for example, a detected, high-resolution form of the respiration signal fails to correspond to a norm).

It has also been shown in the context of the invention that the signal-form of normal breathing in the signal-time diagram is symmetrical, i.e. the rising and falling slopes of a breathing signal measured by distance change according to the invention are disposed symmetrically with respect to a mean value. It is therefore preferred, according to a refinement of the invention, to associate with the evaluation unit signal-form detection means which, for discrimination from other signals (such as artifacts generated by sensor movement, body position signals or cardiac motions) detect with high accuracy and low sensitivity to interference the presence of respiratory activity and further improve display accuracy.

According to a further, preferred refinement (best mode) at least two pairs of sensor units are provided which, in a manner further preferred, in each case span intersecting distances (e.g. approximately at a right-angle) and irradiate the thorax or abdominal area. The respiration-induced, locally (and in some cases temporarily) different thoracic movements can be accounted for especially advantageously in this way and evaluated for still more accurate measurement, e.g. by summation or subtraction of the signals obtained from the two pairs of sensors.

In addition, it is in general included within the present invention to align the sensor units of a given pair of sensor units either in such a way that a connecting line runs outside or along a periphery of the thorax and/or the abdominal area, or to cause the connecting line to pass longitudinally or diagonally through the thorax and/or the abdominal area.

According to a preferred refinement of the invention it is provided, in addition to the respiration-induced signal captured and outputted according to the invention, to capture a heart rate signal of the person to be monitored, this being done in the context of the invention likewise by evaluation of the distance signal obtained through the distance measurement according to the invention. As has advantageously been shown, cardiac activity (having a frequency in a range of typically approx. 1 Hz) also gives rise to periodic movements of the thorax, although the signals can, in the context of the invention, be reliably discriminated in terms of frequency and/or amplitude from the distance signals characteristic of respiration. Additional active monitoring of cardiac activity, in combination with respiration monitoring, therefore not only makes it possible to increase, for example, the diagnostic value of the respiration signal itself, but also allows reliable detection of further critical states of the person, such as sleep apnea or respiratory sinus arrhythmia, thereby allowing any required counter-measures to be taken in good time. Advantageously, there is no necessity for additional sensors for heartbeat detection which, in addition to incurring equipment costs and causing potential problems in fixing them to the patient, would present additional obstacles to a common signal evaluation process using a respiration-dependent signal.

According to a further preferred refinement of the invention it is provided that the first distance signal is evaluated to identify signal changes caused by shocks such as those produced by walking, running or hopping of the person, which, as has been found in the context of the present invention, can also be reliably detected and discriminated from the respiration display signal (especially because, in the case of typical step frequencies in the range of approx. 2.5 Hz, the signals can already be reliably distinguished in their frequency range from the changes in the first distance signal characteristic of breathing and cardiac activity). An additional, active monitoring of step frequency made possible by this refinement of the invention therefore also permits states of the physical activity of the person, such as the training state, and dependences between heart rate, respiration frequency and step frequency, to be reliably detected and analyzed, and subsequent diagnostic measures to be taken. If heart rate signals and step frequency signals are in the same range, they can be discriminated by different amplitudes.

According to a further preferred refinement of the invention it has emerged that a generating curve of an envelope of the respiration display signal, and in particular the upper and lower limit values of this curve (which correspond to a maximum and a minimum distance between the pair of sensor units), characteristically change when the person changes his/her position, for example, in a sleep position—turning, for example, from lying on their back to lying on their side. According to a suitable refinement, an evaluation of these generating curve parameters over a typical period of several minutes therefore additionally makes it possible to derive position data relating to the person from the distance signal.

The present invention is especially suited to use in conjunction with a portable unit co-operating with a base station for data transmission which, an a manner further preferred, is effected wirelessly. The present invention makes it possible to provide the units for data acquisition and evaluation made available according to the invention, which are usually realized by means of suitably programmable controllers, in a portable, battery-powered housing which can be carried about continuously by the person monitored and which makes possible permanent monitoring of respiratory activity, the physical activity of the person and heart rate. Included here is the compilation of a respiration and stress profile (sleep, stress) and observation of respiration as a function of various parameters.

It should be clear that an instrument and a method are created by the present invention which are not only adapted rapidly to distinguish critical from normal breathing states in a simply-evaluated and highly reliable manner (therefore making it possible both to provide rapid assistance and to avoid superfluous dispensing of medication); in addition, through a portable realization of the invention an extremely advantageous instrument for increasing flexibility and convenience in the monitoring of respiratory activity is provided.

As is also achieved by the present invention, a combined analysis of different body functions including respiration, cardiac activity and physical activity can be generated with simple means, and detailed statements on the general condition of a monitored person can be made.

Further advantages, features and details of the invention are apparent from the following description of preferred embodiments with reference to the drawings, in which:

DETAILED DESCRIPTION

Figure 1:
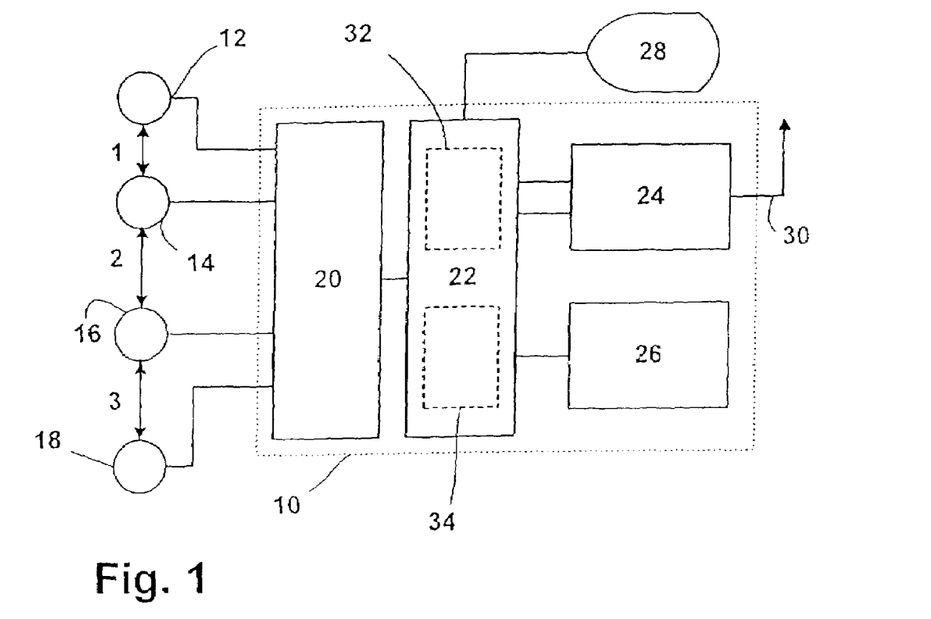
FIG. 1 is a schematic view of the apparatus according to the invention for generating respiration-induced measurement data according to a first embodiment of the invention as a block diagram showing the major functional elements and their interaction.

FIG. 1 clarifies in a block diagram the way in which two pairs of sensor units 12, 14 and 16, 18 of an ultrasonic distance measuring unit 20 are associated inside a portable housing 10, the ultrasonic distance measuring unit 20 emitting in an otherwise known manner—approximately as described in Patent Application DE 42 14 523 referred to above—a corresponding signal suitable for further evaluation on the basis of travel time differences during changes in a distance 1 (between sensor units 12, 14) and a distance 3 (between sensor units 16, 18; in addition, a third distance 2 between a sensor unit of the first pair and a sensor unit of the second pair is captured).

In concrete terms, as is shown in FIG. 1, an evaluation and outputting unit 22 is connected to the output of the distance measuring unit 20 and generates the respiration display signal, which it sends to a display unit 28, preferably a monitor, as a reaction to the distance measurement signal (formed by summation or as a difference signal) of the unit 20 by suitable frequency filtering (preferably effected by calculation from the signal curve) in the range of 0.1 to 0.5 Hz. The evaluation unit is configured for additionally generating a pulse display signal which is generated as a reaction to the detected changes in the first distance signal caused in terms of frequency, amplitude and/or signal shape by the human heartbeat, in particular, in a frequency range of between 0.8 and 2.5 Hz.

In parallel thereto a digital signal pattern of the respiration display signal is stored for later evaluation or correlation with other measurement value curves in a memory unit 26, and a connection of the respiration monitor, as shown in FIG. 1 and realized in the simplest manner, to a wirelessly-connected base station by means of a transmission antenna 30 takes place via a communication unit 24 shown only schematically (and realized in practice, for example, by a currently-used GSM mobile phone unit) for further monitoring and evaluation. The memory unit comprises analysis and storage means associated with the evaluation unit, which are configured for electronically storing the respiration display signal and for detecting a change in terms of amplitude, frequency and/or signal form of the respiration display signal. The analysis and storage means are configured for generating a correlation signal between the respiration display signal and the pulse display signal.

The measuring device and the evaluation unit are components of a portable battery-powered unit 10 which is connectable to a stationary base unit by a wireless data connection for transmission of the display signal and/or further signals. The evaluation unit is configured for additionally detecting a change in the first distance signal generated by running or hopping of the person, and to determine a stepping or hopping frequency therefrom. Furthermore, the evaluation unit is configured for detecting a generating curve of the envelope of the first distance signal over a time interval which is long in comparison to a breathing frequency, and for determining a change in a lower and/or upper limit value of said generating curve.

Figure 2:
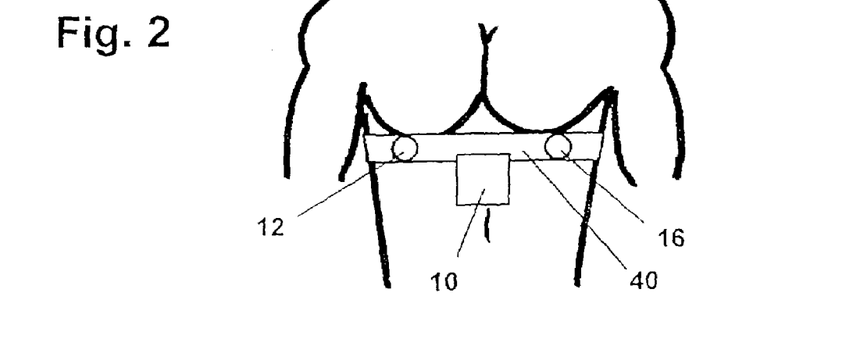
FIG. 2 is a schematic illustration showing an anterior view of the body of a person with the apparatus according to FIG. 1 attached.
Figure 3:
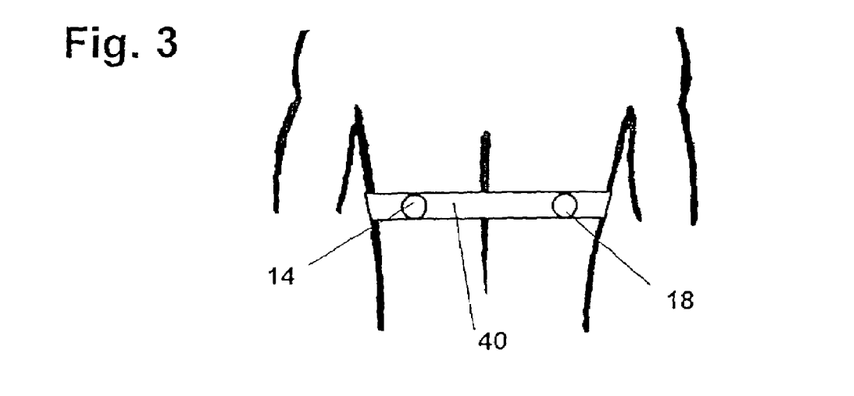
FIG. 3 is a posterior view according to FIG. 2.

FIGS. 2 and 3 show how the apparatus shown schematically in FIG. 1 is operated in practice. A belt 40 is attached in the thoracic area to the schematically illustrated body of a patient, with which belt 40 both the housing 10 and the four sensors 12 to 18 can be so attached to the body of the person that said sensors 12 to 18 can cooperate for reciprocal distance measurement.

Referring now to FIGS. 4 to 9, a number of possible ways of attaching both one and two pairs of sensor units to the body in the manner sketched in FIGS. 2, 3, so that signals well suited to evaluation are attainable, will be discussed by way of example below. In the illustrations of FIGS. 4 to 9 the sensors of one or two pairs of sensor units are in each case represented as circles, and the arrows connecting these circles mark the distances relevant to distance measurement or the generation of distance signals. The illustrations are horizontal cross-sections through the thoracic area at the level of the belt 40 in FIGS. 2, 3, a spinal column 42 being indicated schematically in the posterior area and the heart 44 in the left anterior area.

Figure 4:
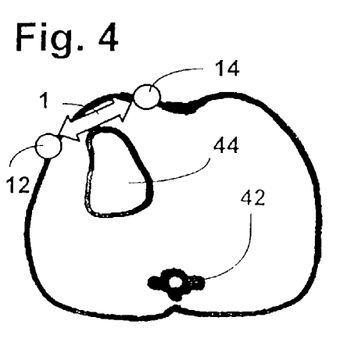
FIGS. 4 to 9 are different schematic illustrations showing the fixing of one or two pairs of sensor units and the definition of the first distance, in the form of pairs of schematic sectional views through the upper part of a human body showing the contracted and the expanded state of the lung.
Figure 5:
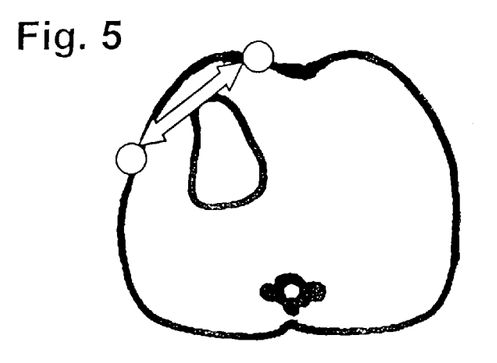

FIG. 4 clarifies schematically the fixing of only one pair of sensor units jointly to an anterior thoracic area of the person so that the length marking the distance (arrow 1) is located on the periphery of the body. Whereas the contracted state of the thorax is shown in FIG. 4, the sensor units are attached in a corresponding manner in FIG. 5, but here the thorax is expanded after inspiration.

Figure 6:
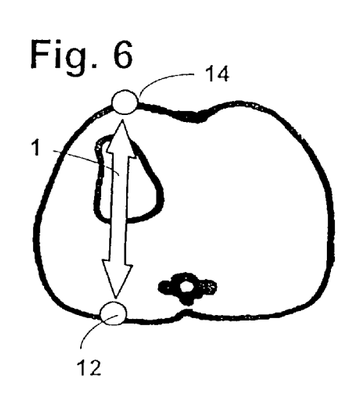
Figure 7:
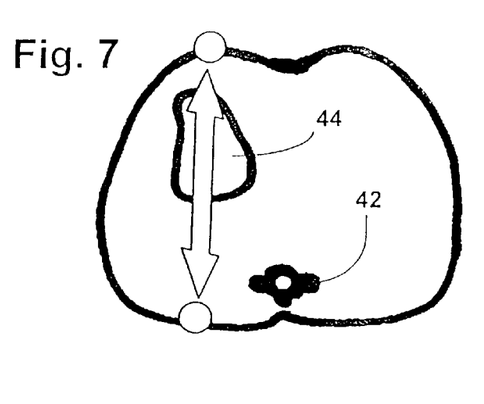

FIGS. 6 and 7 (contracted and expanded state) clarify an alternative manner of fixing a pair of sensors. In this case a first sensor of the pair is arranged in the anterior thoracic area and the second in the posterior area, so that the length (arrow 1) marking the distance extends through the body. The increased distance between the sensors achieved thereby makes it possible in some cases to achieve a further improved resolution of the respiration-induced distance signal as compared to the illustration in FIGS. 4, 5.

Figure 8:
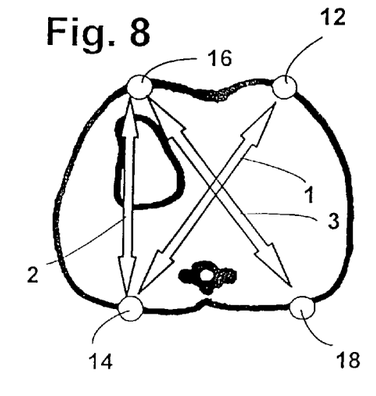
Figure 9:
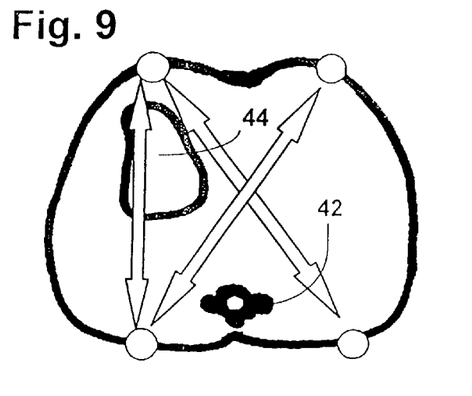

FIG. 8 shows a configuration having two pairs of sensor units which are arranged crosswise in the manner shown in the thoracic and back area; to this extent the sensor arrangement in the sectional views according to FIG. 8, FIG. 9 (again in the contracted and expanded states) corresponds to the sensor arrangement shown in FIGS. 2 and 3 and to the designation of the distances 1, 2, 3 between the individual sensors according to FIG. 1. Here, use is also made of the fact that an additional measurement distance 2 is formed between the sensor units 14 (of the first pair 12, 14) and 16 (of the second pair 16, 18), which can be realized in practice either by means of ultrasonic sensors having a plurality of sensor elements (crystals), by a plurality of sensors fixed in one place, or by a connection and evaluation such that in each case one transmission element is always opposite one receiving element (for example, in the illustration according to FIGS. 8 and 9, 12 could be a transmitting element and 14 a receiving element, 16 could again be a transmitting element and 18 a receiving element, so that a transmission-reception path for evaluation is also formed between 14 and 16).

Through appropriate summation or subtraction an optimized signal resolution can be achieved, especially for the configuration shown in FIGS. 8, 9, which signal resolution, as will be discussed below with reference to signal curves, can be resolved into numerous parameters and detailed information and evaluated in terms going beyond the simple presence of respiration.

Figure 10:
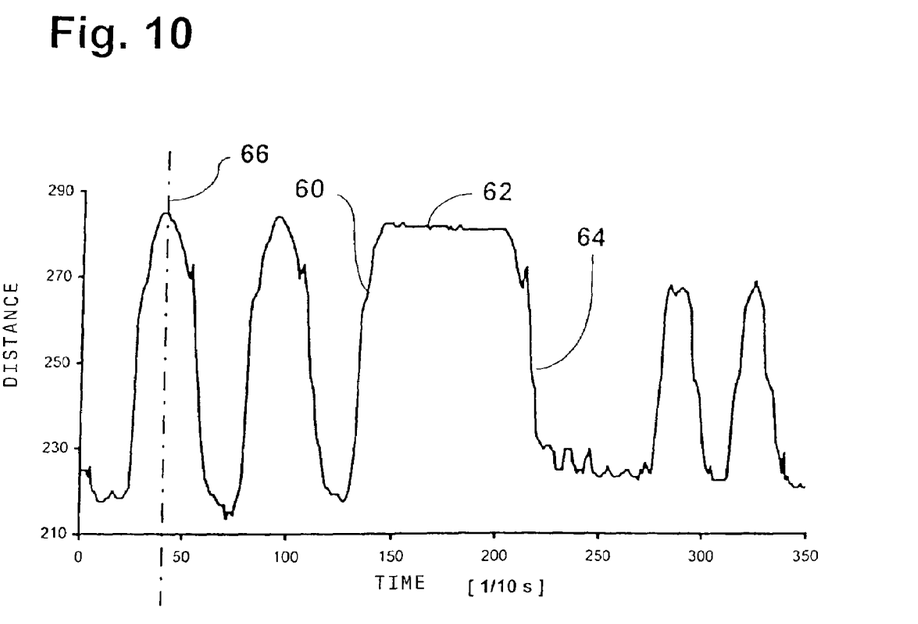
FIG. 10 is a signal/time diagram to clarify the first distance signal and its changes in a rest state.

The representation in FIG. 10 shows a total of five breathing cycles, each breathing cycle being characterized by a rising slope 60, a maximum signal area 62 and a descending slope 64, so that, independently of the depth of breathing—the first two breathing cycles in the illustration according to FIG. 10 represent normal cycles, the middle cycle is a long, especially deep breathing cycle and the two breathing cycles on the right are short, shallower breathing cycles—a symmetrical signal form is produced in the time domain (an axis of symmetry 66 is drawn for the first signal as an example).

Figure 11:
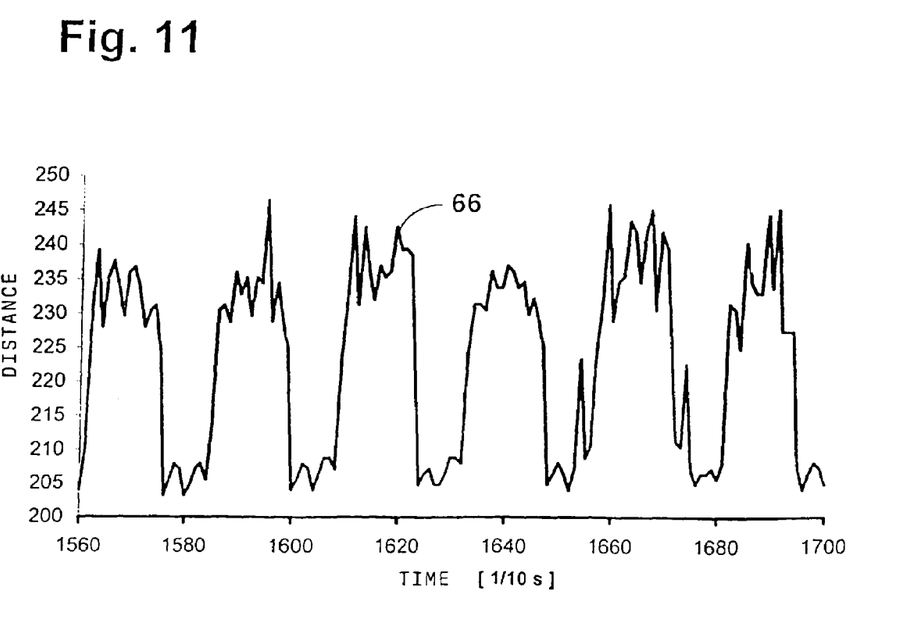
FIG. 11 is an illustration according to FIG. 10, but while the person is running.

As compared to the illustration in FIG. 10, the diagram in FIG. 11, obtained while the person measured was running, shows a characteristic superposing of the respiration signal on a change signal in the range of the running frequency (approx. 2.5 Hz); the signals, which are shorter in comparison to the respiration cycle (although the latter is accelerated by running) are denoted by reference numeral 66 in FIG. 11.

As is shown in FIG. 11, the present invention makes it possible not only to record the respiration signal during physical movement of the person (running, hopping, etc.); because of the impacts occurring upon contact with the ground a slight displacement of the sensor elements in the running or hopping rhythm additionally occurs, these impact peaks being clearly visible in FIG. 11. This superposed signal can, however, be easily separated with regard to both frequency and amplitude from the underlying respiration signal (in order to carry out a separate evaluation), and it also appears possible to transfer this evaluation concept to other applications (cycling, in-line skating or the like) within the scope of the invention.

In the context of the embodiment described according to FIG. 1, evaluation of this stepping frequency is carried out by means of a separate evaluation unit 34 which is associated with the evaluation and display unit 28.

Figure 12:
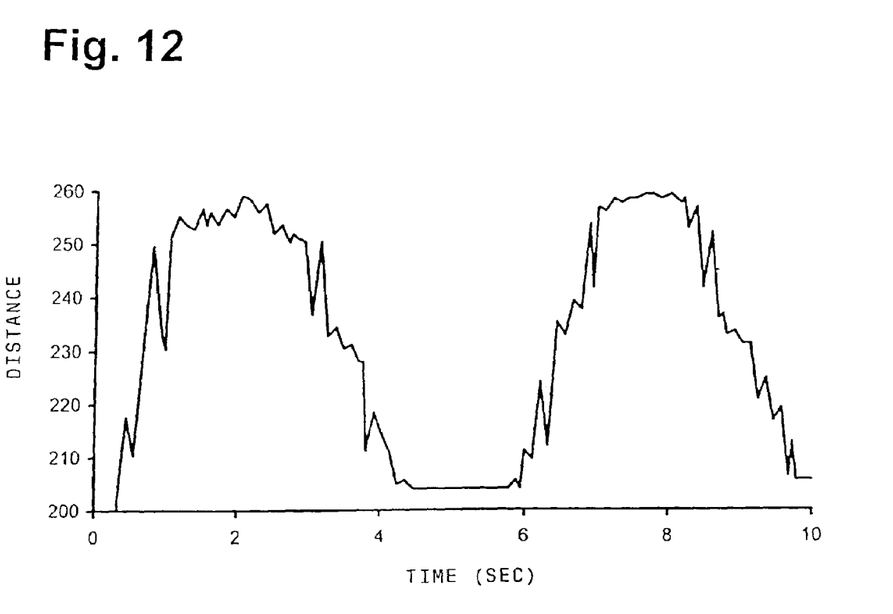
FIG. 12 shows the respiration display signal in enlarged time-resolution to clarify superposed signals (person standing)
Figure 13:
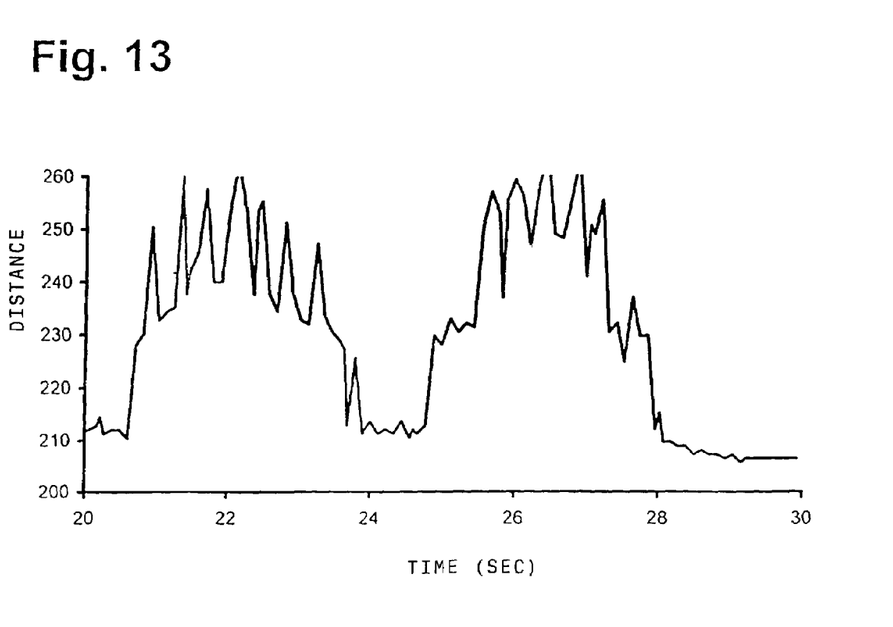
FIG. 13 is a representation analogous to FIG. 12 with the person hopping.

FIG. 12 shows in larger resolution in the signal-time diagram the respiration display signal of a standing person (analogous to FIG. 10); FIG. 13 corresponds with regard to resolution to FIG. 11 and shows respiration display signals when hopping. Superpositions 66 induced by the impacts are again clearly seen.

Figure 14:
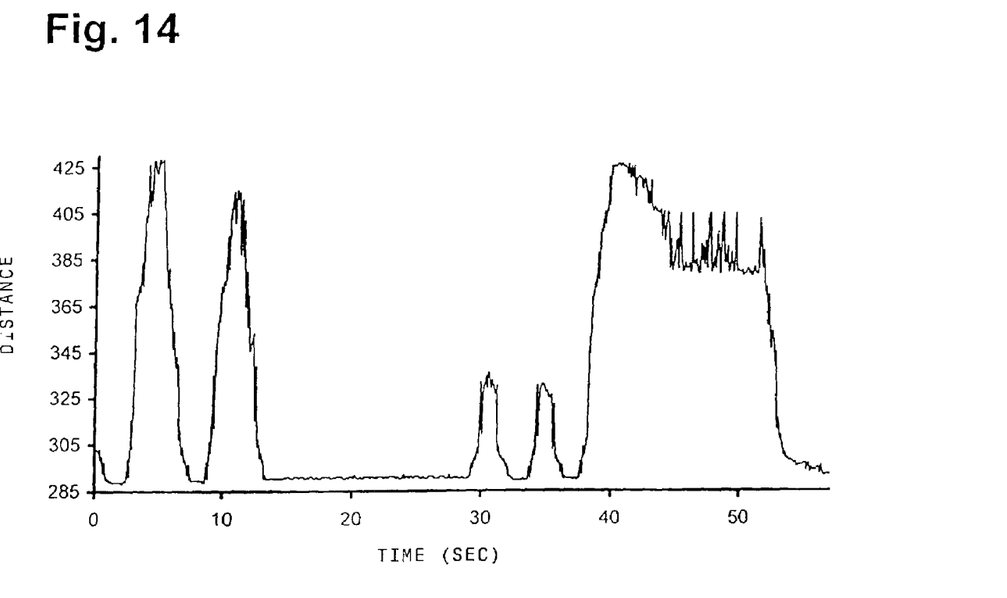
FIG. 14 is a representation analogous to FIGS. 10 to 13, but including various respiration processes and a crossed sensor arrangement analogous to FIGS. 8, 9.

FIG. 14 illustrates a respiration display signal using a sensor arrangement (as in FIGS. 6, 7 and FIGS. 8, 9) in which the effective distance between a pair of sensor units is maximized to improve signal resolution. With his improved resolution the depth of breathing, in particular, can be recognized and distinguished. Thus, the breathing cycles located on the left in FIG. 14 show a waveform characteristic of deep breathing; the following, signal-free time interval corresponds to the pause in breathing after expiration, the following two signals of lower height correspond to normal (less deep) breathing, and the extended and high signal pulse located on the right corresponds to a deep inspiration and subsequent holding of the breath.

Figure 15:
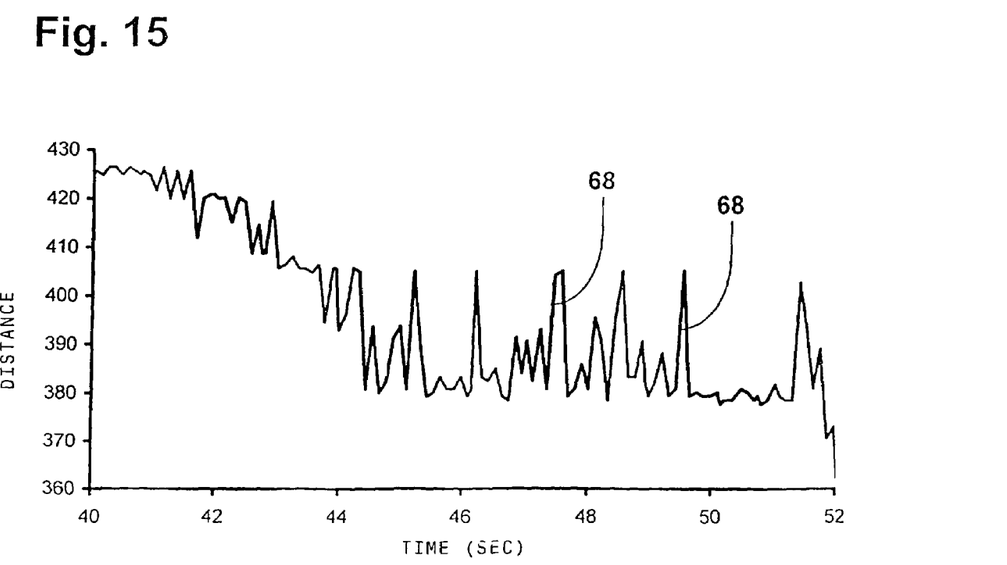
FIG. 15 is an enlarged illustration of a section of the right-hand portion of the signal curve of FIG. 14.

FIG. 15, which shows an enlargement of a section of the deep and sustained breathing cycle located on the right in FIG. 14, clarifies how superposed heartbeat pulses 68 are recognizable in the signal and can be additionally detected and evaluated by suitable discrimination of frequency and/or amplitude. For this purpose a separate discrimination and evaluation unit 32, which detects heart rate in a manner known as such by (preferably numerical) evaluation of a signal curve as in FIG. 15, is associated with the evaluation and outputting unit 22 in FIG. 1.

Figure 16:
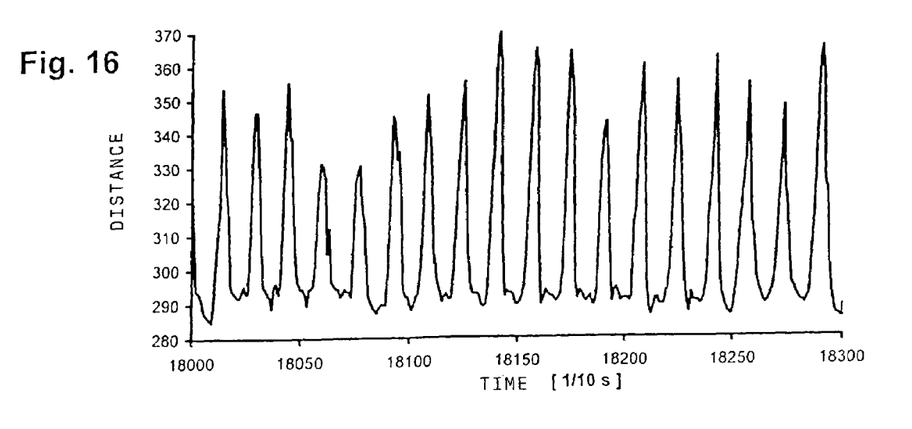
FIG. 16 is a signal/time diagram to clarify the respiration display signal during sporting activity (skating); sensor arrangement according to FIG. 8, FIG. 9.
Figure 17:
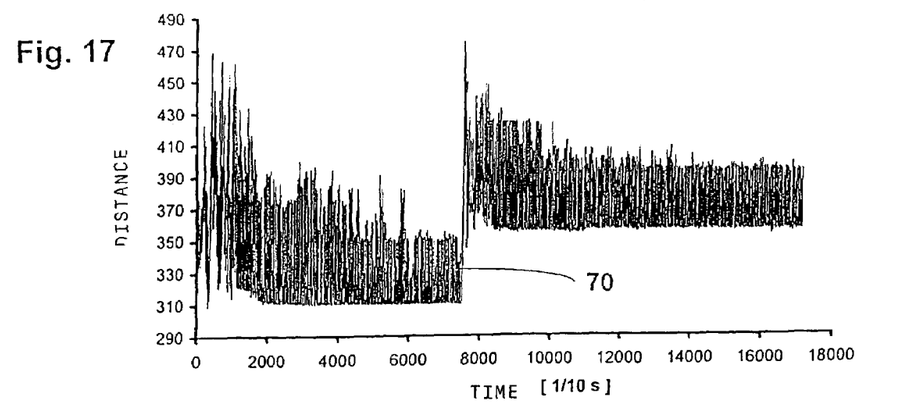
FIG. 17 is a signal/time diagram of a recording over approx. 50 minutes of measurement data for a sleeping person with change of the sleeping position.
Figure 18:
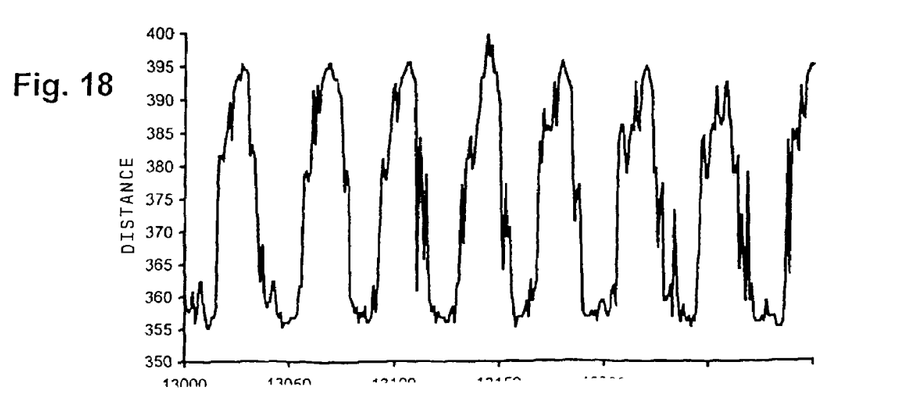
FIG. 18 is an enlarged representation of a section of the view according to FIG. 17 showing the sleep display signal during sleep.

FIG. 16 shows a further example of a respiration display signal during sporting activity (here: skating), while FIG. 17 (long-time measurement over approx. 50 minutes) and FIG. 18 (resolution from FIG. 17 in individual respiration cycles) illustrate breathing signals of a person while asleep.

As has been interestingly shown by (preferably numerical) evaluation of the envelope-generating curve over a period of several minutes according to FIG. 17, position changes of the sleeper (e.g. turning from the back to the side position) give rise to a characteristic jump (reference numeral 70 in FIG. 17) in the envelope-generating curve of the respiration display signal or, more precisely, cause the minimum distance to change abruptly and permanently. Accordingly, through appropriate (preferably numerical) evaluation of the envelope-generating curve such a position change of the sleeper can be detected from the distance signal, which is present in any case, and can be included in further evaluations as a basis for diagnostic purposes.

It can be seen from a consideration of the examples of embodiments and applications, therefore, that the present invention offers potential for a large number of possible applications; these extend from long-time respiration measurement and long-time activity measurement through a taking account of respiration, pulse and movement data in biofeedback and in stress management, through controlled breathing exercises for pregnant women, pace counting while jogging, monitoring of respiration disorders of the most diverse kinds (including monitoring of SIDS, sudden infant death syndrome) to the identification of circulation parameters under stress (including energy conversion measurement), such as the pulse-respiration quotient, all of which is achieved through the evaluation of a single distance signal, admittedly of high-resolution and therefore highly informative, obtained according to the present invention. In addition to the frequency and depth of breathing (where a connection with pulmonary volume exists), therefore, respiration variability can also be detected as a determinable value; through suitable positioning of the sensor units differences between the efficiency of the right and left pulmonary lobes, differences between diurnal and nocturnal activities with regard to breathing, pulse, etc., position changes during sleep, stepping frequency and heart rate (in order to deduce the energy conversion of the person from a combination of breathing and heart rate) and a relationship between abdominal breathing and thoracic breathing, can likewise be detected as determinable values.

The invention claimed is:

1. An apparatus for generating measurement data concerning respiration-related movements of the abdominal wall and/or the thorax of a person, comprising at least one first pair of sensor units which are on an intermediate layer at a first distance from each other when the intermediate layer is fixed on the skin on a thoracic or abdominal area of the person, a measuring device connected to the first pair of sensor units and configured for detecting signals of the sensor units which are capable of electrical evaluation and for generating a first distance signal corresponding to said first distance and changes in same to a second distance signal corresponding to the changes in distances between the sensors as a result of respiratory related movements of the person, the measuring device includes means for outputting the first distance signal in the frequency range of respiration, an evaluation unit is connected to the output of the measuring device and is so configured for evaluating pulsed and/or waveform changes of the first distance signal that periodic signal changes of a frequency in the range between 0.5 and 0.1 Hz can be detected, distinguished in terms of frequency, amplitude or signal form from periodic changes of the first distance signal to the second distance signal caused by the human heartbeat and outputted as a respiration display signal which can be electronically displayed or further evaluated, wherein the evaluation unit is configured for additionally detecting a change in the first distance signal generated by running or hopping of the person, and to determine a stepping or hopping frequency therefrom.

2. An apparatus according to claim 1, wherein the evaluation unit includes means for detecting a signal form of change in the first distance signal, the signal form detecting means being so configured that the respiration display signal is outputted only as a reaction to a signal form of change which is symmetrical in time.

3. An apparatus according to claim 1 or 2, wherein at least one second pair of sensor units connected to the measuring device and configured for detachable fixing on the skin on the thoracic or abdominal area of the person and spaced apart by a second distance.

4. An apparatus according to claim 3, wherein the evaluation unit is configured for summation or subtraction of the first distance signal with respect to a second distance signal outputted by a second pair of sensor units.

5. An apparatus according to one of claims 1, 2 and 4, wherein the evaluation unit is configured for additionally generating a pulse display signal which is generated as a reaction to the detected changes in the first distance signal caused in terms of frequency, amplitude and/or signal shape by the human heartbeat, in a frequency range between 0.8 and 2.5 Hz.

6. An apparatus according to claim 5, wherein analysis and storage means associated with the evaluation unit, which are configured for electronically storing the respiration display signal and for detecting a change in terms of amplitude, frequency and/or signal form of the respiration display signal.

7. An apparatus according to claim 6, wherein the analysis and storage means are configured for generating a correlation signal between the respiration display signal and a pulse display signal.

8. An apparatus according to claim 7, wherein the measuring device and the evaluation unit are components of a portable, battery-powered unit which is connectable to a stationary base unit by a wireless data connection for transmission of the display signal and/or further signals.

9. An apparatus according to claim 1, wherein the evaluation unit is configured for detecting a generating curve of the envelope of the first distance signal over a time interval which is long in comparison to a breathing frequency, and for determining a change in a lower and/or upper limit value of said generating curve.

10. An apparatus according claim 9, wherein the sensor units take the form of ultrasonic sensors.

11. A method for generating measurement data concerning respiration-related movements of the abdominal wall and/or the thorax of a person for operating the apparatus according to claim 1 wherein the steps:
  continuous measurement of a first distance between two first sensors attached on the skin of the person on a thoracic or abdominal area;
  evaluation of electronic signal changes in the first measurement signal corresponding to changes in the first distance, and
  outputting of a respiration display signal as a reaction to a periodical signal change in the range between 0.1 and 0.5 Hz.

12. A method according to claim 11, wherein the steps:
  continuous measurement of at least one second distance between two second sensors attached on the skin of the person on the thoracic or abdominal area;
  evaluation of electronic signal changes in a second measurement signal corresponding to changes of the second distance, and
  numerical combining of the first and second measurement signals for generation of a difference signal or sum signal therefrom.

13. A method according to claim 11 or 12, wherein the step:
  detection of changes in the first distance within a period duration and a signal pattern corresponding to a movement of the abdominal wall or the thorax determined by heartbeat, and outputting of a pulse display signal as a reaction thereto.

14. An apparatus for generating measurement data concerning respiration-related movements of the abdominal wall and/or the thorax of a person, comprising at least one first pair of sensor units which are configured for detachable fixing on the skin on a thoracic or abdominal area of the person and are spaced apart by a first distance, and comprising a measuring device connected to the first pair of sensor units and configured for detecting signals of the sensor units which are capable of electrical evaluation and for generating a first distance signal corresponding to said first distance and changes in same, the measuring device includes means for outputting the first distance signal in the frequency range of respiration, an evaluation unit is connected to the output of the measuring device and is so configured for evaluating pulsed and/or waveform changes of the first distance signal that periodic signal changes of a frequency in the range between 0.5 and 0.1 Hz can be detected, distinguished in terms of frequency, amplitude or signal form from periodic changes of the first distance signal caused by the human heartbeat and outputted as a respiration display signal which can be electronically displayed or further evaluated wherein the evaluation unit includes means for detecting a signal form of change in the first distance signal, the signal form detecting means being so configured that the respiration display signal is outputted only as a reaction to a signal form of change which is symmetrical in a time domain, wherein the evaluation unit is configured for additionally detecting a change in the first distance signal generated by running or hopping of the person, and to determine a stepping or hopping frequency therefrom.

15. An apparatus according to claim 14, wherein at least one second pair of sensor units connected to the measuring device and configured for detachable fixing on the skin on the thoracic or abdominal area of the person and spaced apart by a second distance.

16. An apparatus according to claim 15, wherein the evaluation unit is configured for summation or subtraction of the first distance signal with respect to a second distance signal outputted by a second pair of sensor units.

17. An apparatus according to claim 14, wherein the evaluation unit is configured for additionally generating a pulse display signal which is generated as a reaction to the detected changes in the first distance signal caused in terms of frequency, amplitude and/or signal shape by the human heartbeat, in a frequency range between 0.8 and 2.5 Hz.

18. An apparatus according to claim 17, wherein analysis and storage means associated with the evaluation unit are configured for electronically storing the respiration display signal and for detecting a change in terms of amplitude, frequency and/or signal form of the respiration display signal.

19. An apparatus according to claim 18, wherein the analysis and storage means are configured for generating a correlation signal between the respiration display signal and a pulse display signal.

20. An apparatus according to claim 19, wherein the measuring device and the evaluation unit are components of a portable battery-powered unit which is preferably connectable to a stationary base unit by means of a wireless data connection for transmission of the display signal and/or further signals.

21. An apparatus according to claim 14, wherein the evaluation unit is configured for detecting a generating curve of the envelope of the first distance signal over a time interval which is long in comparison to a breathing frequency, and for determining a change in a lower and/or upper limit value of said generating curve.

22. An apparatus according claim 21, wherein the sensor units take the form of ultrasonic sensors.

23. A method for generating measurement data concerning respiration-related movements of the abdominal wall and/or the thorax of a person for operating the apparatus according to claim 14 wherein the steps:

continuous measurement of a first distance between two first sensors attached on the skin of the person on a thoracic or abdominal area;

evaluation of electronic signal changes in the first measurement signal corresponding to changes in the first distance, and outputting of a respiration display signal as a reaction to a periodical signal change in the range between 0.1 and 0.5 Hz.

24. A method according to claim 23, wherein the steps:

continuous measurement of at least one second distance between two second sensors attached on the skin of the person on the thoracic or abdominal area;

evaluation of electronic signal changes in a second measurement signal corresponding to changes of the second distance, and numerical combining of the first and second measurement signals for generation of a difference signal or sum signal therefrom.

25. A method according to claim 23, wherein the step:

detection of changes in the first distance within a period duration and a signal pattern corresponding to a movement of the abdominal wall or the thorax determined by heartbeat, and outputting of a pulse display signal as a reaction thereto.

* * * * *